United States Patent [19]

Ikemoto et al.

[11] Patent Number: 4,894,793
[45] Date of Patent: Jan. 16, 1990

[54] CALORIE CALCULATOR WITH MENU RETRIEVAL FUNCTION

[75] Inventors: Yutaka Ikemoto; Akiyoshi Yamashita, both of Nara, Japan

[73] Assignee: Sharp Kabushiki Kaisha, Osaka, Japan

[21] Appl. No.: 728,888

[22] Filed: Apr. 30, 1985

[30] Foreign Application Priority Data

May 10, 1984 [JP] Japan ................... 59-94367

[51] Int. Cl.⁴ .......... G06F 15/42; G06F 3/00; G06F 13/00
[52] U.S. Cl. ............... 364/709.03; 364/413.29
[58] Field of Search ........... 364/709, 710, 715, 413, 364/705, 709.03, 709.02, 710.02, 710.11, 413.29, 709.01, 715.01

[56] References Cited

U.S. PATENT DOCUMENTS

| 4,095,274 | 6/1978 | Gordon | 364/715 |
| 4,117,542 | 9/1978 | Klausner et al. | 364/709 |
| 4,244,020 | 1/1981 | Ratcliff | 364/715 |
| 4,321,674 | 3/1982 | Krames et al. | 364/715 |
| 4,354,260 | 10/1982 | Planzo | 364/709 |
| 4,380,802 | 4/1983 | Segar et al. | 364/900 |
| 4,385,291 | 5/1983 | Piquet | 364/706 |
| 4,481,508 | 11/1984 | Kamei et al. | 340/365 VL |
| 4,575,804 | 3/1986 | Ratcliff | 364/715 |
| 4,670,853 | 6/1987 | Stepien | 364/705 |
| 4,686,624 | 8/1987 | Blum et al. | 364/413 |
| 4,751,668 | 6/1988 | Aihara | 364/710 |

FOREIGN PATENT DOCUMENTS

| 2901174 | 8/1980 | Fed. Rep. of Germany | 364/715 |
| 59-33570 | 2/1984 | Japan | 364/715 |
| 60-118972 | 6/1985 | Japan | 364/413 |

Primary Examiner—Gary V. Harkcom
Assistant Examiner—Dale M. Shaw
Attorney, Agent, or Firm—Birch, Stewart, Kolasch & Birch

[57] ABSTRACT

A calorie calculator comprises a keyboard for manually controlling the operation of the calorie calculator, a memory for storing a plurality of items of menu data and the corresponding calorie data, a retrieval circuit responsive to the operation of the keyboard for retrieving a particular item of menu data and the corresponding calorie data from the memory, and a display responsive to the retrieval circuit for displaying the particular item of the menu data and the corresponding calorie data.

6 Claims, 6 Drawing Sheets

CALORIE CALCULATOR WITH MENU RETRIEVAL FUNCTION

BACKGROUND OF THE INVENTION

THe present invention relates to a calorie calculator and, more particularly, to a calorie calculator with a menu retrieval function.

Conventionally, there has been proposed a type of calorie calculator for calculating the calorie depending on the type of food. However, the name of the food must be referred to in a guide book, so that the calculation procedure for counting the calories is rather troublesome because of the necessary use of the guide book.

SUMMARY OF THE INVENTION

Accordingly, it is an object of the present invention to provide an improved calorie calculator suitable for calculating the calories consumed by retrieving the names of the menu items.

It is another object of the present invention to provide an improved calorie calculator for calculating the calories consumed by retrieving the names of the menu items, the method of cooking, and the food material involved to retrieve the calorie data corresponding to the menu, so that the calorie data of the menu can be totally calculated.

Briefly described, in accordance with the present invention, a calorie calculator comprises keyboard means for manually controling the operation of the calorie calculator, memory means for storing a plurality of items of menu data and the corresponding calorie data, retrieval means responsive to the operation of the keyboard means for retrieving a particular item of menu data and the corresponding calorie data from the memory means, and output means responsive to the retrieval means for outputting the particular menu data and the calorie data.

BRIEF DESCRIPTION OF THE DRAWINGS

The present invention will become more fully understood from the detailed description given hereinbelow and the accompanying drawings which are given by way of illustration only, and thus are not limitative of the present invention and wherein.

DESCRIPTION OF THE PREFERRED EMBODIMENT

Figure 1:
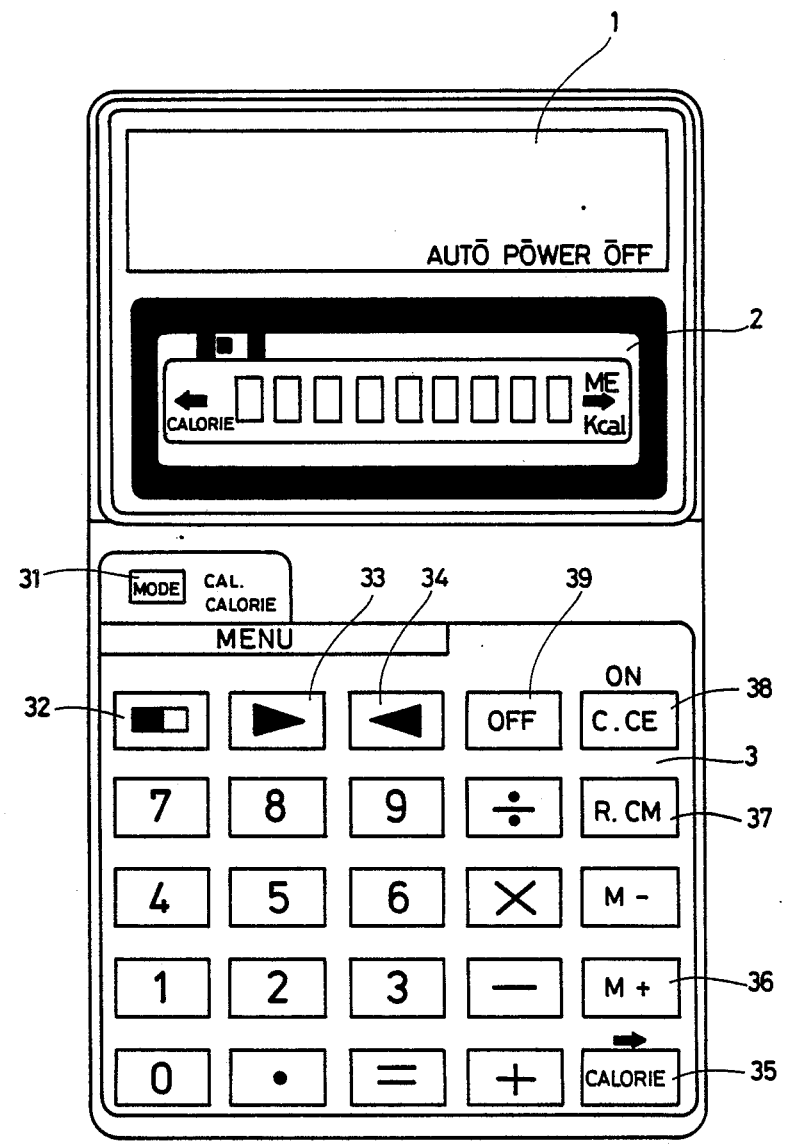
FIG. 1 is a plan view of a calorie calculator according to the present invention.

FIG. 1 is a plan view of a calorie calculator according to the present invention.

The calorie calculator of FIG. 1 comprises a body 1, a display 2, and a keyboard 3. The display 2 is provided for displaying the name of a menu item retrieved and the corresponding calorie data. It may be composed of a dot matrix type liquid crystal display of several digits, each of 5×7 dots. The keyboard 3 contains a mode selection key 31, menu retrieval keys 32, 33, and 34, a calorie data retrieval key 35, a memory key 36, a memory clear key 37, a clear entry key and power-on key 38, and a power-off key 39.

The mode selection key 31 is operated to select either an arithmetic calculation mode or a calorie calculation mode. Each time the key 31 is operated, either mode is alternatively selected. The menu retrieval keys 32 through 34 are operated in the calorie calculation mode to retrieve the name of the menu item. The first retrieval key 32 is operated to recall the heading letters of the menu items aligned in the order of the Japanese syllabary. When it is continuously operated, the letters of the Japanese syllabary heading a plurality of menu items are subsequently retrieved. The second retrieval key 33 is operated to select the next menu item data. The third retrieval key 34 is operated to select previous menu item data and operates to select data in an opposite direction from the first retrieval key 32 and the second retrieval key 33.

The calorie key 35 is operated to retrieve the calorie data equivalent to the searched menu. The memory key 36 is operated in the calorie calculation mode to store the total of the calorie data in a memory. This key 36 is also operated in the arithmetic calculation mode to store the arithmetic data in another memory. The memory clear key 37 is operated at the first actuation to recall the contents of the memory. It is operated for a second time to cancel the contents of the memory. The clear entry key 38 is operated to execute a clear and entry operation. It is also operated to turn the calculator power on. The power-off key 39 is operated to switch off this calculator.

FIGS. 2(A) through 2(F) are some typical examples of displaying the heading letter of menu items by operating the key switches to retrieve the menu items.

Figure 2:
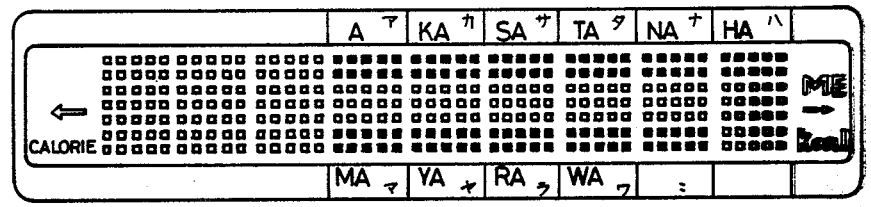
FIGS. 2(A) through 2(F) show examples of displaying the heading letters of a plurality of menus used for the present invention.
Figure 2:
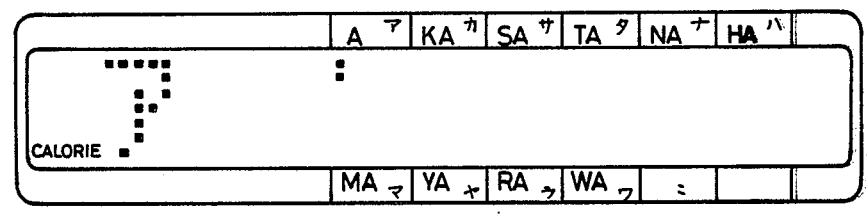
Figure 2:
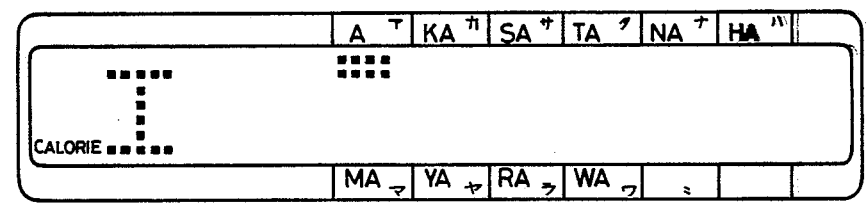
Figure 2D:
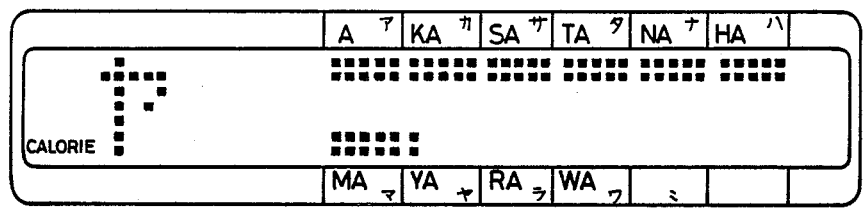
Figure 2E:
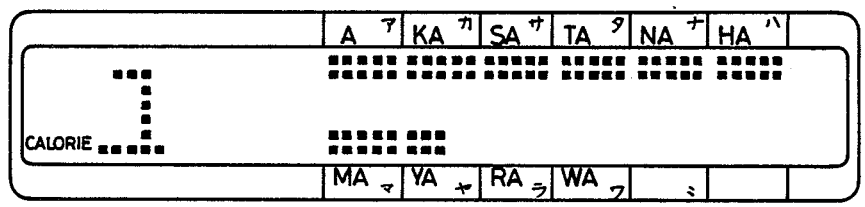
Figure 2F:
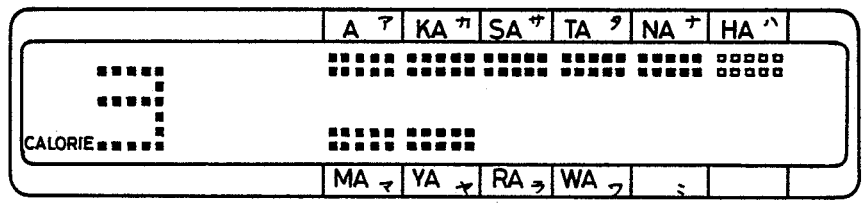

FIG. 2(A): Some dots in all of a plurality of display digits in the display 2 are switched on. Symbols of "CALORIE", "→", "←", "M", "E", and "K cal" are contained within the display 2.

FIG. 2(B): As a heading letter of a particular menu item, a Japanese letter corresponding to a Roman character "a" is displayed near the symbol of "CALORIE". A single heading letter of each menu item is displayed at the upper part of the display 2. The serial number of this Japanese letter, corresponding to "a", in the column containing this Japanese letter in the Japanese syllabary is designated by two dots in the column of "A" in the display 2.

FIGS. 2(C) through 2(F): Japanese heading letters each equivalent to Roman characters "e", "ya", "yu", and "yo" are displayed in each highest digit in FIGS. 2(C) through 2(F), respectively, together with having their column positions and the serial numbers in the columns in the Japanese syllabary displayed in the respective columns in the display 2.

I. Arithmetic Calculation Mode

This mode is a typical arithmetic calculation mode in an ordinary calculator. The calorie calculator of FIG. 1 is operated as an arithmetic calculator with 8 digits and a single memory. In the calculator of FIG. 1, a clear key (C) and a clear entry key (CE) is combined in a single key of the key 38. A recall memory key (RM) and a clear memory key (CM) is combined in a single key of the key 37.

II. Calorie Calculation Mode (1) Food Material Name Retrieval Method 1: The menu item retrieval keys 32 through 34 are used to retrieve the name of the food material to retrieve the corresponding calorie data.

(EXAMPLE 1: to retrieve the calorie data corresponding to a food material of ("Japanese radish")

No. 1:
KEY OPERATION: key 38
DISPLAY: 0.
COMMENT: If no power, the calculator is switched on.

No. 2:
KEY OPERATION: key 31
DISPLAY: CALORIE_
COMMENT: The calorie calculation mode is selected.

No. 3:
KEY OPERATION: key 32
DISPLAY: CALORIE "a"

No. 4:
KEY OPERATION: The key 32 is continually operated.
DISPLAY: CALORIE "ta"
COMMENT: The Japanese heading letter "ta" of "Japanese radish" is displayed by the operations of nos. 3 and 4. When overrun, the key 34 is operated to back.

No. 5:
KEY OPERATION: key 33
DISPLAY: CALORIE "Japanese radish": One Slice →
COMMENT: The name of the food material "Japanese radish" is retrieved and displayed.

No. 6:
KEY OPERATION: key 35
DISPLAY: CALORIE 10K cal
COMMENT: The calorie data of the food material are displayed.

TABLE I

Thereafter, by operating the key 33, the food materials following the "Japanese radish" can be subsequently retrieved and displayed.

(2) Food Name Retrieval Method 2:
The key 33 only is operated to retrieve the name of the food to obtain the corresponding calorie data.

(EXAMPLE: to retrieve the calorie data equivalent to "Savory Pancakes")

No. 1:
KEY OPERATION: key 38
DISPLAY: CALORIE_
COMMENT: The contents of the display are canceled.

No. 2:
KEY OPERATION: key 33
DISPLAY: CALORIE "ICE CREAM": One →
COMMENT: The first data of the calorie data are retrieved and displayed.

No. 3:
The key 33 is continually operated. p0 DISPLAY: CALORIE "Japanese Hotchpotch": One Helping →
COMMENT: The menu data are retrieved subsequently.

No. 4:
KEY OPERATION: key 34
DISPLAY: CALORIE "Savory Pancakes": Bits of (Continued) →
COMMENT: When overrun, the key 34 is operated.

No. 5:
KEY OPERATION: key 35
DISPLAY: CALORIE (Continuing) Meat 470K cal

TABLE II (3) To Sum Up the Calorie Data of the Menu Items (EXAMPLE: to retrieve the sum of the menu items of "Rice", "Miso Soup (Bean Paste Soup)", "Chinese Noodle Soup", "Orange Juice", and "Sukiyaki")

No. 1:
KEY OPERATION: key 38
DISPLAY: CALORIE_
COMMENT: The display contents are canceled.

No. 2:
KEY OPERATION: key 32
DISPLAY: CALORIE "a"

No. 3:
KEY OPERATION: The key 32 is continually operated.
DISPLAY: CALORIE "co"
COMMENT: The heading letters of the menus are searched in Nos. 2 and 3.

No. 4:
KEY OPERATION: key 33
DISPLAY: CALORIE COFFEE, BLACK TEA →

No. 5:
KEY OPERATION: key 33
DISPLAY: CALORIE "Cola": One Can →

No. 6:
KEY OPERATION: key 33
DISPLAY: CALORIE "Rice": One Rice Ball →
COMMENT: In Nos. 4 through 6, the names of the menus are searched.

No. 7:

---

KEY OPERATION: key 36
M
DISPLAY: CALORIE 220.
K cal
COMMENT: The calorie data of "Rice" are stored into a memory.

---

No. 8:
COMMENT: The operations of Nos. 1 through 5 are repeated.

No. 9:

| KEY OPERATION: key 33 | |
|---|---|
| DISPLAY: CALORIE "Miso Soup (Bean Paste Soup)" One Cap→ | M |

No. 10:

| key 36 | |
|---|---|
| DISPLAY: CALORIE 40. | M K cal |

No. 11:

| KEY OPERATION: key 36 | |
|---|---|
| DISPLAY: CALORIE 460. | M K cal |

The operations of Nos. 9 through 11 are repeated in connection with "Chinese Noodle Soup", "Orange Juice", and "Sukiyaki" to sum up their corresponding calorie data using the key 36 in a memory.

No. 12:

| KEY OPERATION: key 37 | |
|---|---|
| DISPLAY: CALORIE 1380. | M K cal |
| COMMENT: The total calorie data are displayed in the display 2. | |

TABLE III

To cancel the contents of the memory, the key 37 is twice operated in succession.

To cancel the contents of the display 2, the key 38 is twice operated in succession.

(4) To Arithmetically Operate the Calorie Data of the Foods:

(EXAMPLE: To add 150K cal to the calorie data of "Hamburger" to give the sum)

No. 1:
KEY OPERATION: key 33
DISPLAY: CALORIE "Hamburger": →
COMMENT: The keys 32 and 33 are operated to retrieve the food.

No. 2:
KEY OPERATION: plus key "+"
DISPLAY: CALORIE 260.K cal
COMMENT: The calorie data of "Hamburger" are retrieved.

No. 3:
KEY OPERATION: numeral keys "1", "5", and "0"
DISPLAY: CALORIE 150.K cal
COMMENT: The numerical data as the calorie data are inputted as an arithmetic calculator.

No. 4:
KEY OPERATION: equal key "="
DISPLAY: CALORIE 410.K cal

COMMENT: The added calculation results are displayed.

TABLE IV

To sum up the calorie data in the memory, the key 36 "M+" is operated in place of the equal key "+". The sum up results can be displayed by operating the key 37.

(EXAMPLE: to know the calorie data corresponding to five "Caramels")

No. 1:
KEY OPERATION: key 33
DISPLAY: CALORIE "Caramel": One →
COMMENT: The keys 32, 33, and 34 are operated to retrieve the foods.

No. 2:
KEY OPERATION: product key "×"
DISPLAY: CALORIE 20.K cal
COMMENT: The calorie data equivalent to one "Caramel" are retrieved and displayed.

No. 3:
KEY OPERATION: numeral key "5"
DISPLAY: CALORIE 5.

No. 4:
KEY OPERATION: equal key "="
DISPLAY: CALORIE 100.K cal
COMMENT: The total of the calorie data by "20"×"5" is obtained.

TABLE V

Similar operations using a subtraction key "−" and a division key "÷" are conducted.

(5) To Sum Up the Calorie Data Together With Arithmetically Operating the Units of the Foods.

(EXAMPLE: to sum up the calorie data in connection with all of the menu items in a day)

BREAKFAST:
a piece and half of toast
Milk 200 cc
Ham and Eggs

LUNCH:
Bowl of rice topped with boiled chicken and eggs
a cup of coffee

DINNER:
10 flies of Oyster
a bowl and half of rice p1 a thick custardy soup p1 a bottle of beer No. 1:
KEY OPERATION: key 33
DISPLAY: CALORIE "Toast": a piece, →

No. 2:
KEY OPERATION: product key "×" and numeral keys "1", ".", and "5"
DISPLAY: CALORIE 1.5
COMMENT: By the operations of Nos. 1 and 2, a piece and half of toast are selected.

No. 3:

| KEY OPERATION: key 36 | |
|---|---|
| | M |

-continued

DISPLAY: CALORIE 300.
K cal
COMMENT: The calorie data are stored into a memory.

No. 4:

KEY OPERATION: keys 32 and 33
M
DISPLAY: CALORIE "Milk": one (continued)→

No. 5:

KEY OPERATION: key 35
← M
DISPLAY: CALORIE (continuing) bottle 118
K cal
COMMENT: In Nos. 4 and 5, the milk of 200 cc is selected.

No. 6:

KEY OPERATION: key 35
M
DISPLAY: CALORIE 118.
K cal
COMMENT: The calorie data are stored into a memory.

Similar operations are conducted in connection with other foods of "Ham and Eggs" etc.

No. 7:

KEY OPERATION: key 33
M
DISPLAY: CALORIE a large bottle of "Beer"→
COMMENT: The calorie data of a bottle of "Beer" are selected.

No. 8:

KEY OPERATION: key 36
M
DISPLAY: CALORIE 247.
K cal
COMMENT: The calorie data are stored into the memory.

No. 9:

KEY OPERATION: key 37
M
DISPLAY: CALORIE 2645.
K cal
COMMENT: The total of the calorie data in a day is calculated and displayed.

TABLE VI

To sum up the calorie data, the key 36 "M+" must be operated. Even when only the key 35 "CALORIE" is operated, the calorie data are displayed, but are not summed.

As shown in Nos. 4 and 5 of TABLE II and Nos. 4 and 5 of TABLE III, if the name of the menu item cannot be displayed on a single line in the display 2 in such a manner that "Savory Pancakes": Bits of Meat→470K cal, the "CALORIE" key 35 is operated to divide the display contents. Further, as shown in No. 3 of TABLE V, after either of the function keys such as the product key "×" and the division key "÷" is operated, the input of a numeral enables the symbol of "K cal" to be erased.

Figure 3:
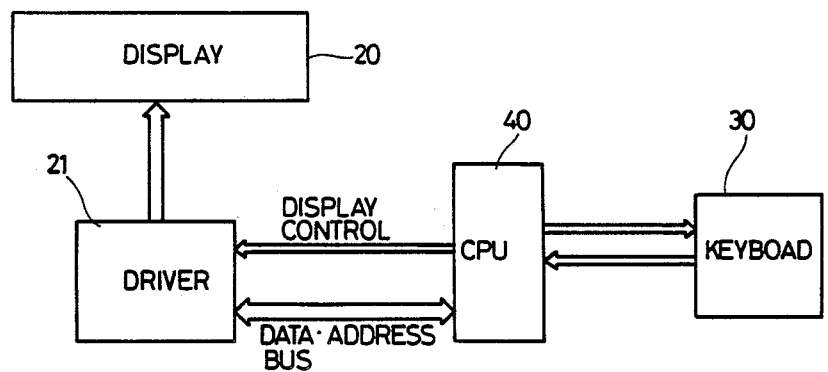
FIG. 3 is a block diagram of the calorie calculator according to the present invention.

FIG. 3 is a block diagram of the calorie calculator of FIG. 1.

The circuit of this calorie calculator comprises two Large Scale Integrated Circuits (LSIs). A central processing unit (CPU) 40 is a single chip microprocessor of 4 bits. This CPU 40 is provided for storing a system program, the menu item data, and the calorie data. The CPU 40 serves to control the display and key input. A display 20 relates to the display 2 of FIG. 1. A driver 21 is provided for driving the display 20.

Figure 4:
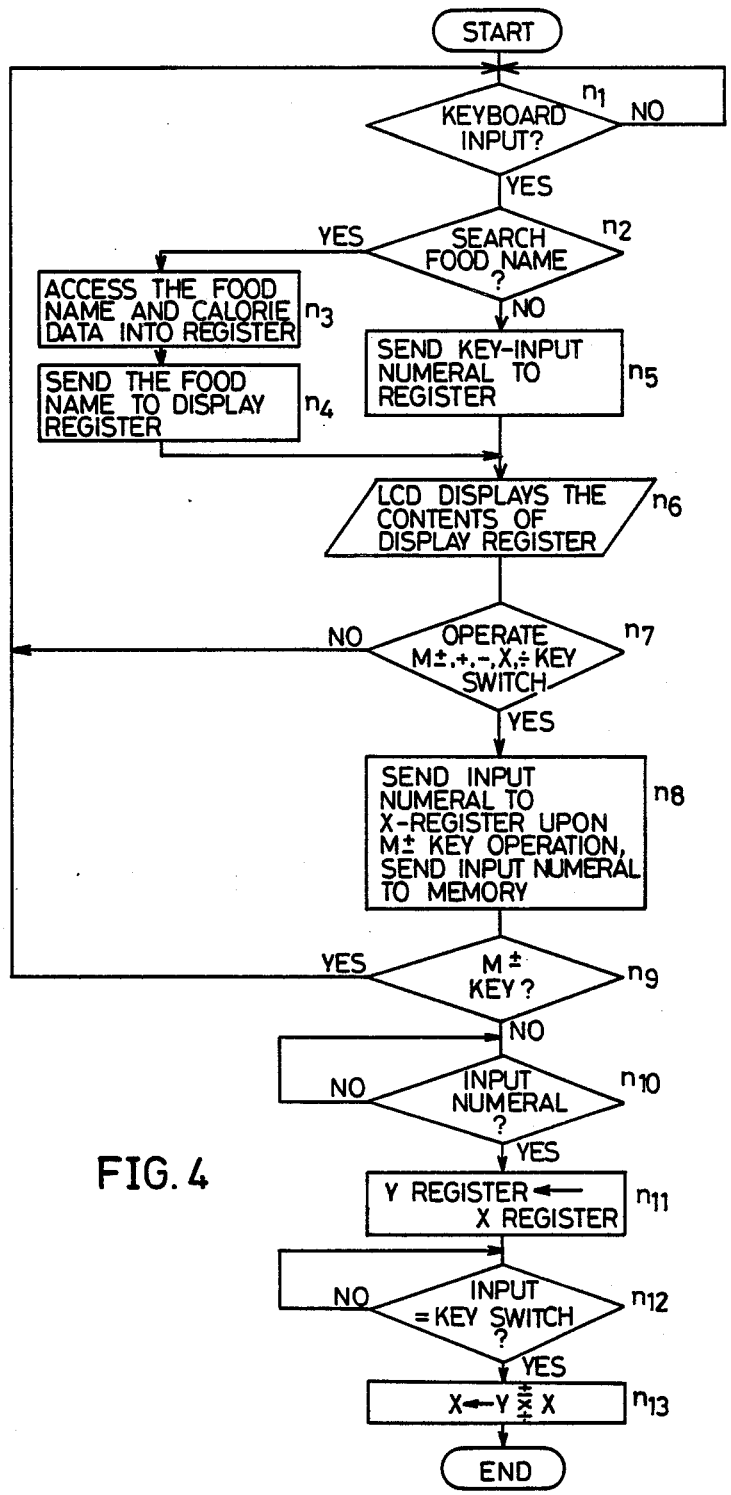
FIG. 4 is a flow chart of the calorie calculation algorithm of a calorie calculation mode in the calorie calculator.

FIG. 4 is a flow chart of the algorithm of the calorie calculation mode.

The first data as the calorie data are stored into an X register. After one of the four function keys for the four fundamental rules of the arithmetics is operated and before the second data of the calorie data are inputted, the contents of the X register are forwarded into a Y register. The second data are loaded into the X register. To obtain the calculation results, the results which are obtained by adding the contents of the Y register to the contents of the X register (or, either of subtracting, producting, and dividing) are forwarded into the X register.

With reference to FIG. 4, the calorie calculation mode is conducted by storing, in place of the first numeral data, the calorie data equivalent to the menu item retrieved by the menu item name searching operation.

Steps n1 and n2: Upon inputting the key operation of the keyboard 3, the type of the operated key is detected to detect whether it is the menu item retrieval keys 32 through 34 or not.

Step n3: In accordance with the type of the operated key, the name of the menu item and its corresponding calorie data are inputted into the X register.

In connection with the retrieval or search operation of the menu items, the operations in steps n1 through n7 are equal to the input of operated values in the four fundamental rules of the arithmetics or the input in the numeral in the arithmetic calculation mode with a memory.

Step n5: This step is executed to directly input the numeral by key input operation rather than inputting the numeral by the menu retrieval.

Steps n10 and n11: These are executed to input an operation value.

Steps n12 and n13: These are executed to detect whether to operate the equal key 37 =" and the corresponding calculation.

Steps n2 through n7: These are executed to input the first data in the calorie calculation mode.

Steps n10 through n13: These are executed to input the second data in the calorie calculation mode.

Step n6: This is selected to store the character data pattern in the CPU. The character pattern is displayed.

Step n11: This is selected to add the symbol of "K cal" after the addition key "+" or the subtraction key "−" is operated.

Figure 5:
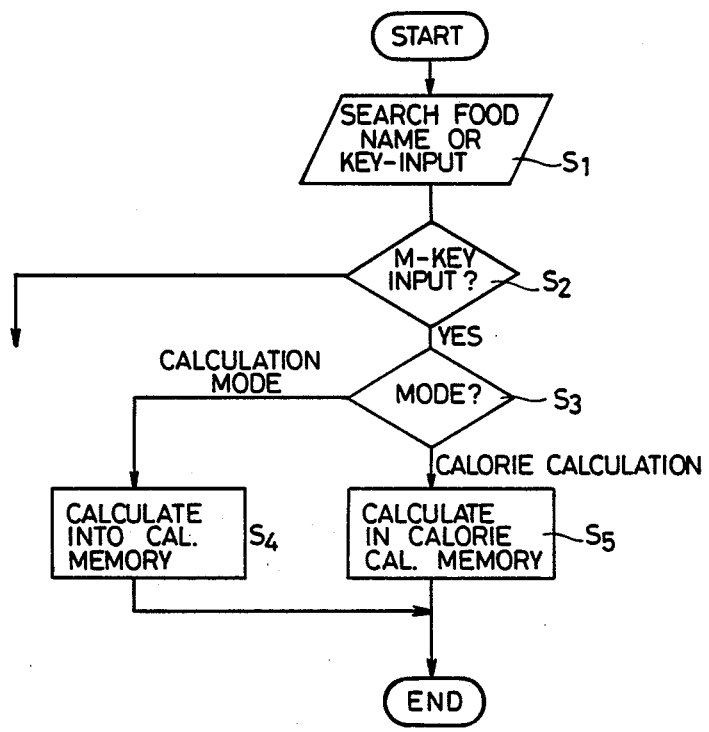
FIG. 5 is a flow chart of the operation of a memory in the calorie calculator in an arithmetic calculation mode and a calorie calculation mode.

FIG. 5 is a flow chart showing the operation of the memory in the arithmetic calculation mode and the calorie calculation mode.

Step S5: Because the different memories are used depending on the type of the arithmetic calculation mode and the calorie calculation mode, either memory cannot be destroyed even when the mode switching and the memory contents are enabled.

Figure 6:
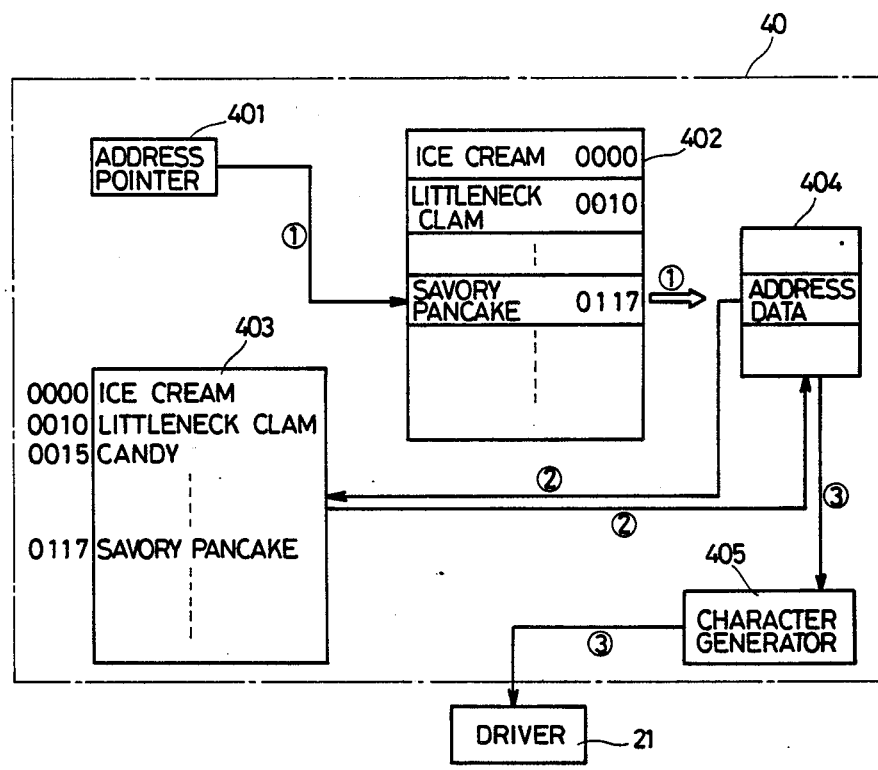
FIG. 6 shows a method of retrieving the name of the menu item or food in a central processing unit (CPU).

FIG. 6 is a schematic illustration of retrieving the menu item name using the CPU 40.

The CPU 40 comprises an address pointer 401, a menu address table 402 composed of a read only memory (ROM), a read only memory (ROM) 403 for storing the menu and the corresponding calorie data, and random access memory (RAM) 404 for storing address data, and a character generator 405.

The menu items are retrieved as related to the numerals representative of retrieval procedures in FIG. 6 as follows:

① Upon the operation of the menu item retrieval keys 32 through 34, the data in the address table 402 directed by the relating address pointer 401 are loaded into the RAM 404.

② Because the location of the RAM 403 equivalent to the address data stored in the RAM 404 contains the menu item data, the menu item data are written-in from the RAM 403 to the RAM 404.

③ Because the data stored in the RAM 404 are represented in the respective character data, the character data are translated into the corresponding display patterns with reference to the character generator 405. The display patterns are forwarded into the driver 21.

According to the calorie calculator of the present invention, the calorie data of the retrieved menu items can be summed up in the memory. The calorie data retrieved by the operation of the menu item retrieval keys 32 through 34 are summed up in the memory by operating the "CALORIE" key 35. The total data can be retrieved and displayed by operating the key 37 once. The contents of the memory can be canceled by operating the key 37 twice in succession. Because the calorie calculation mode is independent on the arithmetic calculation mode, two memories are peculiar to the two modes. Even when either memory is used in either of the two calculation modes, the contents of the other memory for the other calculation mode are unchanged.

In response to the key input of the numeral after the actuation of the product key "×" and the division key "÷", the symbol of "K cal" is erased while the numeral input after the actuation of the addition key "+" and the subtraction key "−" enables the illumination of the symbol of "K cal" as shown in FIG. 4.

It may be further possible that it is announced automatically whether the contents of the memory exceed a predetermined value or not. In the flow chart of FIG. 4, in steps n7 and n8, in response to the actuation of the key 36 "M+", the sum of the calorie data are transferred into the memory in step n8. The contents of the memory are compared with the predetermined value. Depending on the results of the comparison, it can be announced that the sum of the calorie data exceeds the predetermined value. An announcement means for this purpose comprises a display or an voice synthesizer.

As described above, according to the present invention, the calorie memory is provided for storing a plurality of menu items, particular foods and the corresponding calorie data. The calorie data relating to the menu items and the particular foods can be retrieved.

While only certain embodiments of the present invention have been described, it will be apparent to those skilled in the art that various changes and modifications may be made therein without departing from the spirit and scope of the present invention as claimed.

What is claimed is:

1. A calorie calculator comprising:
   keyboard means for manually controlling the operation of the calorie calculator;
   said keyboard means comprises first menu item retrieval key means for selecting the heading letters of menu items, second menu item retrieval key means for selecting the names of menu items, and third menu item retrieval key means for presenting menu item data in reverse order;
   memory means for storing a plurality of items of menu data and the corresponding calorie data;
   retrieval means responsive to the operation of said keyboard means for retrieving a particular item of the menu data and the corresponding calorie data from said memory means; and
   output means responsive to said retrieval means for outputting the particular item of the menu data and the corresponding calorie data.

2. The calculator of claim 1, further comprising sum means responsive to said retrieval means for summing up the calorie data in connection with some items of the menu data.

3. The calculator of claim 1, further comprising comparison means responsive to said retrieval means for comparing the calorie data with a predetermined value, and announcement means responsive to said comparison means for announcing that the calorie data exceed the predetermined value.

4. The calculator of claim 1, further comprising address pointer means for directing the address of said memory means.

5. The calculator of claim 1, wherein said output means comprises display means for displaying the menu data and the calorie data, and character generator means provided for generating a display pattern corresponding to the particular item of the menu data and the corresponding calorie data.

6. A calorie counter comprising
   keyboard means having a plurality of keys for carrying out different functions,
   a mode selection key for selecting a first and a second mode of the calculator,
   a first data memory operated only in the first mode,
   a display means for displaying information,
   a second data memory for storing the menu and the corresponding calorie data,
   said second data memory is operated only in said second mode,
   predetermined memory contents in the second data memory provided in succession to be selected in one or the opposite direction by actuating keys repeatedly for displaying said memory contents as information on said display means,
   a further key is provided for summing up parts of the memory contents of different memory areas of said second data memory when actuating said further key, and
   a character generator is provided for generating a display pattern on said display means corresponding to the particular memory contents.

* * * * *